United States Patent [19]

Khayat

[11] 4,096,734

[45] Jun. 27, 1978

[54] METHOD OF REMOVING HEADSPACE VOLATILES AND ANALYSIS THEREOF

[75] Inventor: Ali Khayat, Carlsbad, Calif.

[73] Assignee: Ralston Purina Company, St. Louis, Mo.

[21] Appl. No.: 760,872

[22] Filed: Jan. 21, 1977

[51] Int. Cl.$^2$ ............................................. G01N 31/08
[52] U.S. Cl. ................................. 73/23.1; 73/421.5 R
[58] Field of Search .................... 73/23.1, 23, 421.5 R; 23/232 R, 232 C, 254 R; 141/52, 59

[56] References Cited

U.S. PATENT DOCUMENTS

| | | | |
|---|---|---|---|
| 2,413,261 | 12/1946 | Stackhouse | 23/232 R |
| 2,786,355 | 3/1957 | Day et al. | 73/421.5 R |
| 3,203,248 | 8/1965 | Stutler et al. | 73/421.5 R |

OTHER PUBLICATIONS

Mendelsohn et al., "Techniques for Collecting Volatile Components from Haddock Fish for Gas Chromatography," *Journal of Food Science*, vol. 31, 1966, pp. 389-393.
Yonezawa et al., "Simple Device for Removing Gas Samples from Sealed Containers for Gas Chromatography," *Food Technology*, Apr. 1963, pp. 134-135.
Nawar et al., "Technique for Collection of Food Volatiles for Gas Chromatography," *Analytical Chemistry*, vol. 32 No. 11, Oct. 1960, pp. 1534-1535.
Stahl et al., "Gas Chromatographic Method for Determining Gases in Headspace of Cans," *Food Technology*, vol. 14, No. 1, Jan. 1960, p. 14.

*Primary Examiner*—Richard C. Queisser
*Assistant Examiner*—Stephen A. Kreitman
*Attorney, Agent, or Firm*—W. Dennis Drehkoff

[57] ABSTRACT

A method of completely removing the volatiles in the headspace area of cans, bottles and other sealed containers which comprises inserting first and second penetrating means into the headspace of the sealed container without prematurely releasing the vacuum of the sealed container, passing a carrier gas into the headspace of the sealed container through said first penetrating means and removing the carrier gas and headspace volatiles from the sealed container through said second penetrating means for analysis.

19 Claims, 4 Drawing Figures

METHOD OF REMOVING HEADSPACE VOLATILES AND ANALYSIS THEREOF

BACKGROUND OF THE INVENTION

Knowledge of the qualitative and quantitative composition of headspace volatiles would help food scientists solve problems associated with canned food storage stability and container corrosion. In canned foods containing proteinaceous materials such as meat and vegetables, amino acids may decompose when subjected to heat and release hydrogen sulfide. This gas may react with the metal of the can and form compounds which may discolor the food and render it oderiferous. Gas chromatography is utilized to analyze hydrogen sulfide for it allows a rapid analysis of gas mixtures associated with canned foods. One common conventional method involves the extraction of juice from an individual food piece and then flushing the gas from the food juice into a cold trap for analysis by gas chromatography. Other methods involve taking a sample of the headspace gas rather than a food piece. A procedure for analyzing hydrogen gas in canned food by gas chromatography is described in *Food Technology* 21 p. 47 (1967). In this method a 0.5 ml sample of the headspace gas of a canned product is taken by a modified air tester. The sample is analyzed in a gas chromatograph using helium as the carrier gas. Unfortunately, this method allows the extraction of small samples of gases and a complete sample containing all headspace gases may not accurately be taken. Another method utilizing gas chromatography is described in *Food Technology* 17 p. 134 (1963), which involves the taking of individual samples by a syringe. A notable limitation of this method is the uncertainty of complete removal of all gases from packed cans. However, none of these methods show a procedure for the removal of all the headspace volatile from a canned food product for analysis.

The present invention represents a significant breakthrough in applying qualitative and quantitative techniques to determine the complete analysis for total headspace volatiles present in a sealed container.

SUMMARY OF THE INVENTION

The present invention comprises a method of analyzing all the volatiles found in the headspace area of cans, bottles and other sealed containers. The process comprises the steps of inserting first and second penetrating means into the headspace of the sealed container without releasing the vacuum of the sealed container, passing a carrier gas into the container through the first penetrating means, withdrawing the carrier gas and all headspace volatiles through the second penetrating means and subjecting the volatiles to qualitative and quantitative analysis.

It is an object of the present invention to provide a method of removing all headspace volatiles from sealed containers.

Another object of the present invention is to provide a method to quantitatively and qualitatively analyze all headspace volatiles in a sealed container.

And yet another object of the present invention is to provide a method for removing and analyzing hydrogen sulfide in canned tuna.

DETAILED DISCUSSION

A knowledge of the qualitative and quantitative composition of headspace gases will help food scientists identify the headspace gas precursors and also help ascertain the relative contribution of gas precursors substances to canned food deterioration. Although many headspace volatiles, such as oxygen, hydrogen, nitrogen, carbon dioxide and carbon monoxide are problematic to food scientists, this invention was conceived and developed largely for the removal and analysis of headspace volatiles, particularly hydrogen sulfide, in canned tuna. Therefore, it will be explained largely with respect to the headspace volatiles found in canned tuna although it can be used for other headspace volatiles in other food products in broader aspects of the invention.

A critical feature of this invention is the ability to remove all or substantially all of the headspace volatiles from the canned product to be tested. The prior art techniques, involving removal of individual samples of headspace volatiles, are not efficient for strict quality control standards.

As previously discussed, the present invention involves the passing of a carrier gas, preferably an inert gas such as nitrogen or helium, through penetrating means into the headspace of a sealed container. First and second penetrating means are utilized in this invention for the introduction of the inert carrier gas and removal of the carrier gas and headspace volatiles. After the inert carrier gas is withdrawn with the total volatiles present in the headspace area of the sealed container, the volatiles may then be collected in a trap for analysis by conventional laboratory qualitative and quantitative techniques. Some of the common techniques known for this purpose involve colorimetric titrations or gas-liquid chromatography and mass spectrometry. The penetrating means for inserting the inert carrier gas into the sealed container as well as the penetrating means used to remove the inert carrier gas and headspace volatiles from the sealed container, must not release the vacuum of the sealed container upon their insertion therein and allow the introduction of air and escape of headspace volatiles. A premature release of the volatiles would accordingly make analysis more difficult.

The flow rate of the carrier gas must be sufficient to remove all the volatiles present in the headspace area of the sealed container. Although not intended to limit the invention, a preferred flow rate of the inert carrier gas would be in the range of about 1 cc/min. to 100 cc/min.

Figure 1:
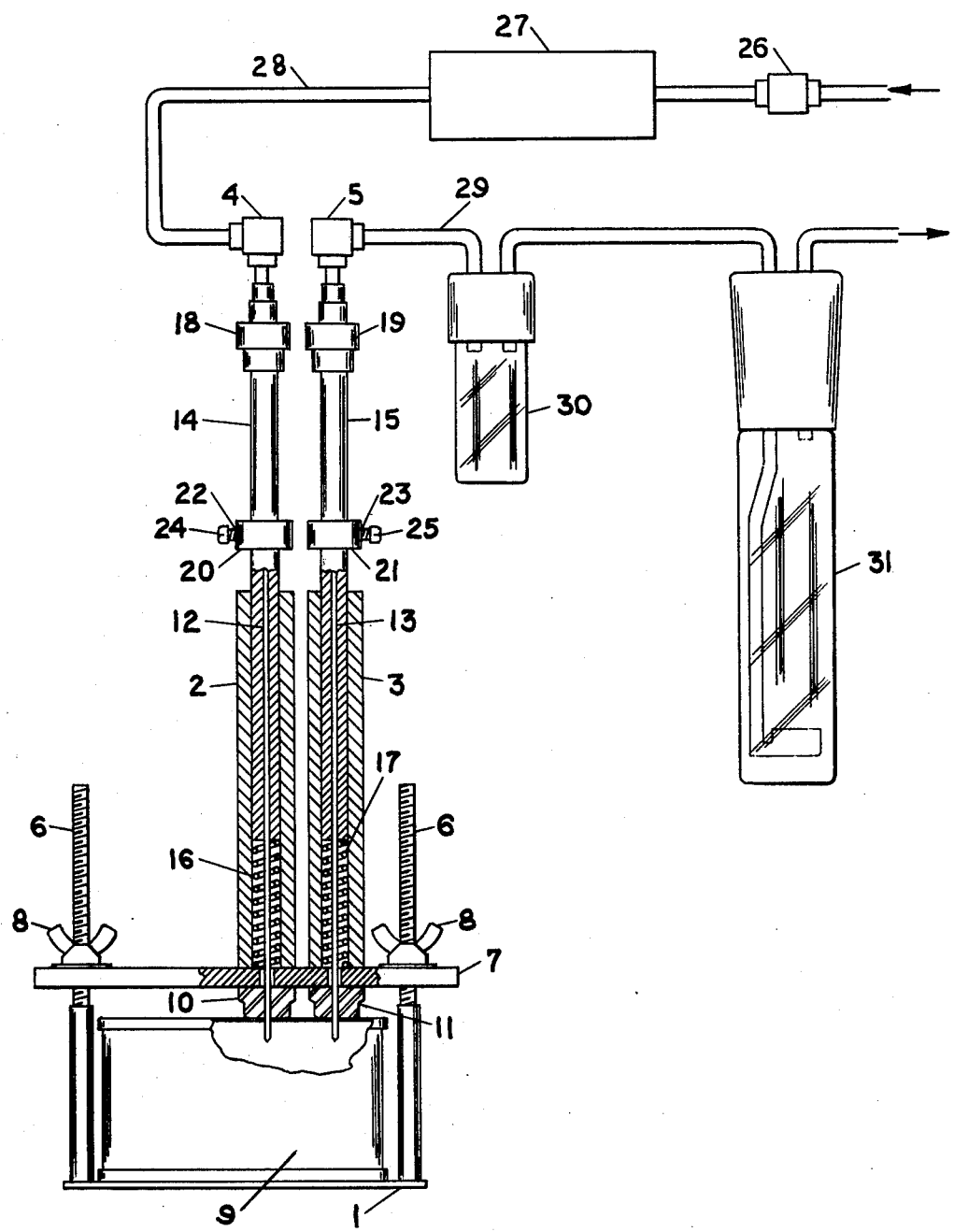
FIG. 1 represents a typical apparatus employed in the instant method of removing and analyzing headspace volatiles.

Referring now to FIG. 1 which is intended to provide a more complete understanding of the total process of the present invention and the relationship of the present improvement to this process, a typical apparatus that can be utilized in the present process is shown. The sampling apparatus illustrated in FIG. 1 is relatively simple, having base plate 1, vertical tubular housings 2 and 3 and three way valves 4 and 5. The sampling apparatus is generally described in U.S. Patent 3,374,678 and that disclosure is herein incorporated by reference. Base plate 1 has bolts 6 for attaching holding plate 7 by wing nuts 8 to secure sealed container 9 in rigid position for the removal of headspace volatiles. Vertical hollow tubular housings 2 and 3 pass securely through plate 7 and contact the lid of sealed container 9 by passing through silicone rubber septums 10 and 11. The silicone rubber septums provide an air tight seal for hollow penetrating means 12 and 13 which pass therethrough. Hollow penetrating means 12 and 13 are placed internally of tubular housing 2 and 3 and extend from valves 4 and 5 to the sealed container 9. The exact size of the penetrating means is not intended to limit the present invention and any standard hollow needle or tubing may be employed. With no intention to limit the invention, hollow penetrating means 12 and 13 will be referred to as needles hereinafter.

The hollow needles are attached to inner sleeves 14 and 15 which are interposed within tubular housings 2 and 3 and supported by springs 16 and 17. FIG. 1 embodies a cut-a-way section of the tubular housings to expose said springs and needles. Handles 18 and 19 are present to provide a grip to manually push the inner sleeves and attached needles into sealed container 9 in longitudinal movement. A collar located at 20 and 21 is disposed on the inner sleeves 14 and 15 and is slideable thereon, there being a radially extending tapped bore 22 and 23 in said collar in which is threadably disposed screw 24 and 25 for securing the collar in adjusted positions on said inner sleeve. The collar provides adjustable means for limiting forward movement of the inner sleeves and hollow needles. The amount of penetration of the can by needles 12 and 13 is limited by adjusting the position of collars 20 and 21 on inner sleeves 14 and 15. When a needle has been forced into a lid of a can, it is held therein by friction. After removal of the headspace volatiles, the needles 12 and 13 are pulled from the can and springs 16 and 17 return the needles and inner sleeves to the normal outermost position.

In operation, a can of tuna is centrifuged for 10 minutes at 900 X G before securing it on base plate 1 by holding plate 7. This centrifugation step is not intended to limit the invention, but is preferred because it moves the liquids present in the container away from the headspace area. An inert carrier gas such as helium or nitrogen is passed through valve 26 and rotameter 27 where it is maintained at a flow rate of about 1 cc/min. to 100 cc/min. in line 28. The exact size of line 28 is not intended to limit the present invention, however, it is preferred that its outside diameter be about 1/16 inch. Valve 4 containing the inert gas in line 28 remains closed at this time. Next, handle 19 is manually gripped and pushed downward towards the can 9, so that outlet needle 13 penetrates the lid of the can and enters the headspace area. Valve 5 remains closed so the vacuum is not released from the can. Inlet needle 12 is then inserted into the headspace area of the can in a similar manner. Valve 4 on the inlet needle is opened to allow the inert gas to fill the needle and release the vacuum of the can. The stream of carrier gas enters the headspace area of the can and valve 5 on outlet needle 13 is then opened. The sequence of inserting penetrating needles 12 and 13 into sealed containers to be sampled is not intended to limit the process of the present invention. Inlet needle 12 may be inserted in the sealed container before the introduction of outlet needle 13, however, care must be taken not to release the vacuum within the sealed container prematurely. The vacuum should be released from the can as the inert carrier gas fills the penetrating means and enters the sealed container. Therefore, valves 4 and 5 must be closed and opened accordingly in the proper sequence. The gas flow is monitored by rotameter 27 and is controlled by valves 4 and 5 in such a manner that no air enters the system. To keep the can at a constant temperature it may be submerged in a water bath at a constant temperature of 25° C. The stream of inert carrier gas and headspace volatiles then passes through line 29 to liquid trap 30. The trap removes any liquids carried over with the volatiles from the can. The inert carrier gas and volatile stream passes into another trap 31 where a composition can be deposited to selectively bind the desired volatile required for analysis. For example, hydrogen sulfide gas reacts with zinc acetate solution by forming a precipitate of zinc sulfide which can readily be identified quantitatively by colorimetric analysis.

Figure 2:
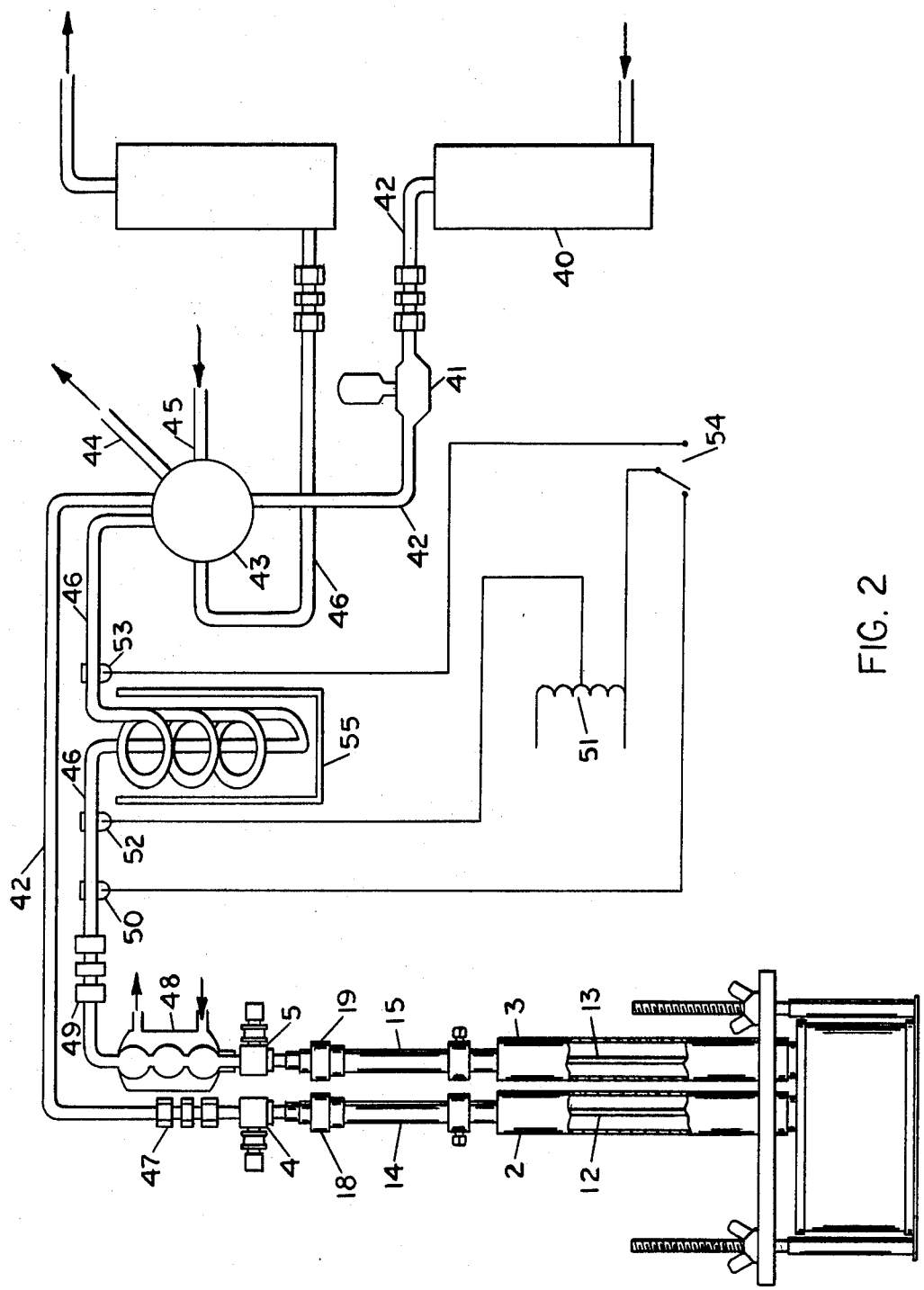
FIG. 2 represents an alternative embodiment of a typical apparatus used in the instant method of removing and analyzing headspace volatiles.

Referring to FIG. 2, an alternate embodiment of the present invention, gas-liquid chromatography analysis is utilized in the noted process. The profiles of headspace volatiles of control and spoiled canned tuna can be quickly determined for quality control purposes by the use of a gas-liquid chromatograph. Further, definitive qualitative and quantitative analysis of the volatiles can be carried out by mass spectrometry or other means after the profiles are traced by gas-liquid chromatography.

The process for passing an inert carrier gas through a sealed container and removing headspace volatiles is similar to the aforementioned process. However, two different inert carrier gases are utilized, one to flush the volatiles from the sealed container, the other to flush the volatiles through the system to the gas-liquid chromatograph. Both inert carrier gases are selected from the group consisting of nitrogen and helium. The first inert carrier gas is passed through rotameter 40 and flow control valve 41 in stainless steel tubing line 42. Line 42 passes through variable switching valve 43 which has access lines to the gas chromatograph 44. Line 45 is a source for the second inert carrier gas. The first inert carrier gas passes through line 42 to thread mounted joint 47 which engages three-way valve 4. The sealed container is prepared for headspace gas analysis as previously described in the first embodiment of this invention. However, the container may be submerged in a water bath at a temperature of about 70° C to insure a constant temperature of the volatiles. After the container is prepared with the insertion of needles 12 and 13, valve 4 is opened to allow the entrance of the inert carrier gas to flush the volatiles through needle 13 into condenser 48 which contains cold water at a temperature of about 2° C. The function of this condenser is to eliminate most of the water vapors present in the volatiles. Condenser 48 must have ingress and egress means for the passage of the cold water, preferably in a vertical arrangement to allow the upward flow of the water. The volatiles then pass through stainless steel egress tubing line 46, through thread mounted joint 49 and are heated to about 80° C by direct resistance heating means 50, or any equivalent heating means. Variable autotransformer 51 controls the direct resistance heating of line 46 at points 50, 52 and 53 which are in turn controlled by single pole, double-throw switch 54. Next, the volatiles enter cold trap 55 immersed in a cold alcohol bath of about −75° C. The cold trap can be made from stainless steel tubing about 1/16 inch in outer diameter and 0.03 inch inside diameter shaped in the form of a coil, about 3 cm. in diameter and 17 cm. long. The volatiles are condensed in cold trap 55 and line 42 is disconnected at thread mounted joint 47 and joined with joint 49. Variable switching valve 43 is then adjusted to lead egress line 46 to gas-chromatograph line 44. Line 45 containing the second inert gas and different from the gas originally present in line 42 is connected to line 42 by said variable switching valve to flush the condensed volatiles from cold trap 55 into line 44 leading to the gas chromatograph. As the volatiles are being flushed from the cold trap, line 46 is heated to about 130° C. by heating means 50, 52 and 53 to insure the complete removal of all the volatiles from the cold trap.

A more complete understanding of the invention can be obtained by referring to the following illustrated examples which are not intended however, to be unduly limitative of the invention.

EXAMPLE 1

The apparatus shown in FIG. 1 was used for the removal of hydrogen sulfide from the headspace of canned tuna. Before the can was placed in the sampling apparatus it was centrifuged for 10 minutes at 900 × gravity in order to pack the material inside the can and increase the space gas volume. The needles were inserted into the can so that the vacuum would not be released and pure nitrogen gas was introduced into the can to flush the headspace volatiles into a glass absorption trap. The gas was supplied at a flow rate of about 5 cc per minute. The absorption trap was equipped with a fritted glass disc of 60 to 70 microns pore diameter and contained a zinc acetate solution. A small glass trap approximately 10 milliliters in volume was placed before the trap to insure that no liquid would enter into the absorption trap. The determination of the sulfide ion concentration was by the methylene blue method found in an article by Sands, A. E.; Grafius, M. A.; Wainwright, H. W.; Wilson, M. W. *The determination of low concentrations of hydrogen sulfide in gas by the methylene blue method.* 1949, U.S. Dept. Interior, Bureau of Mines Rpt. of Investigations, N. 4547; as modified by Prince, C. G. T. *J. Appl. Chem.* 1955, 5, 364. The zinc acetate solution containing dissolved sulfide ions was cooled in an ice water bath and 5 millimeters of a P-aminodimethylaniline solution was added and mixed. This was followed by the addition of 1.0 milliliter ferric chloride solution with further mixing. The solution was taken out of the ice water bath and set aside for 15 minutes along with a reagent blank. The developed color was determined at 746 nm by a Varian Techtron spectrophotometer, model 635.

EXAMPLE 2

Vapor Sampling Apparatus for Gas Chromatography Headspace Volatiles

The alternate embodiment of the present invention is shown in FIG. 2. The flow rate of the incoming nitrogen gas was about 100 cubic centemeters per minute. The volatiles were flushed into a cold trap and the gas lines connected to a helium source. The cold trap was heated for about 4 minutes at 130° C. and volatiles were flushed by the helium into the gas chromatograph.

Figure 4:
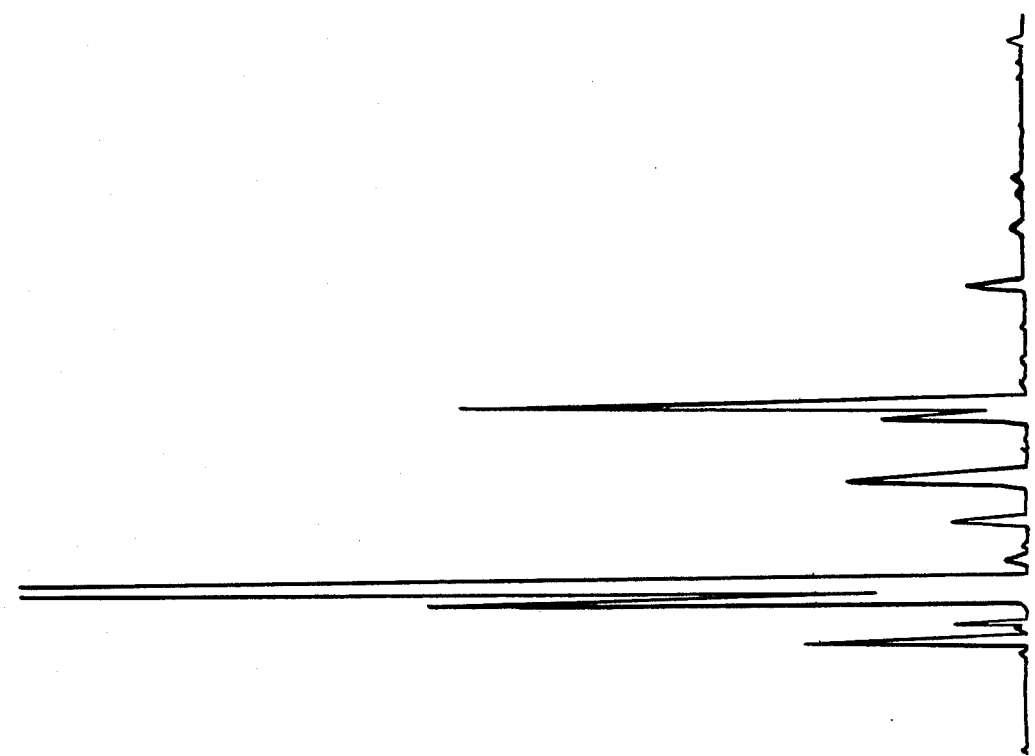
FIG. 4 represents a profile of total volatiles found in canned tuna by a flame ionization detector of a gas chromatograph.
Figure 3:
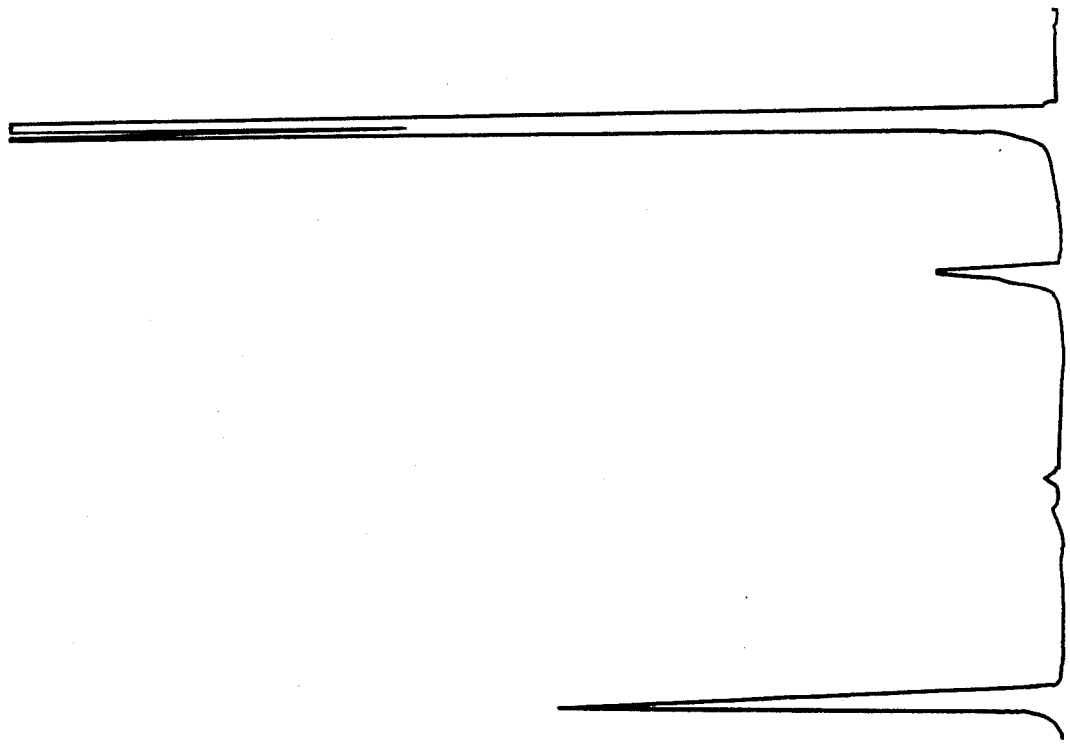
FIG. 3 represents a profile of sulfur containing volatiles found in canned tuna by a flame photometric detector on a gas chromatograph.

The analysis was performed on a Beckman 72-5 model gas chromatograph dual column which was equipped with a hydrogen flame ionization detector. The run was made on a capillary support coated stainless steel column, 400 ft. long and 0.03 inches inside diameter. Flow rates of 17 milliliter per minute helium, 45 milliliter per minute hydrogen, 250 milliliter per minute air and 90 millimeter per minute helium were used throughout the system. All gases were purified by passing them through a gas filter hydropurge. The gas chromatograph oven was programmed in two stages: the first stage was an isothermal step, at 50° C for 4 minutes, and the second stage was temperature programmed from 50° to 100° C for 32 minutes. The injector and the switching valve temperature was 130° C. the detector temperature was 220° C, and the detector line temperature was 135° C. The electrometer sensitivity was set at $1 \times 10^{-10}$ amps. A recorder was attached and a base line drift corrector and a recorder chart speed of 20 cm/hr. was used throughout the experiment. FIG. 3 shows a sulfur containing volatile from canned tuna using a flame photometric detector attached to the gas chromatograph. FIG. 4 shows the profile of headspace gases found in canned tuna with a flame ionization detector attached to the gas chromatograph. These profiles can be used as a point of reference in headspace gas analysis of canned tuna for quality control purposes.

As will be evident to those skilled in the art, a modification of the present invention can be made in view of the foregoing disclosure without departing from the spirit of scope of the present invention.

What is claimed is:

1. A method of removing volatiles present in the headspace area of a sealed container without prematurely releasing the vacuum and said volatiles in said container comprising the steps of:
   (a) inserting a first penetrating means into the headspace area of a sealed container,
   (b) inserting a second penetrating means into said headspace area of said container,
   (c) passing an inert carrier gas into said headspace area of said container through said penetrating means,
   (d) withdrawing said inert carrier gas and volatiles from said headspace area in said container through said penetrating means other than the means utilized for the passing of said inert carrier gas into said container.

2. The method of claim 1 wherein the inert carrier gas is supplied at a flow rate of about 1 to about 100 cc/min.

3. The method of claim 1 wherein the inert carrier gas is selected from the group consisting of nitrogen and helium.

4. The method of claim 1 wherein the sealed container is submerged in water.

5. The method of claim 4 wherein the sealed container is submerged in water at a temperature of about 25° C.

6. The method of claim 1 wherein there is a complete removal of headspace volatiles in the sealed container.

7. The method of claim 1 wherein said first and second penetrating means are hollow.

8. A method of removing and analyzing all the volatiles present in the headspace area of canned tuna without prematurely releasing the vacuum and said volatiles in said container comprising the steps of:

(a) inserting a first penetrating means into the headspace area of said canned tuna,
(b) inserting a second penetrating means into the headspace area of said canned tuna,
(c) passing a carrier gas into said headspace area of said canned tuna through said penetrating means,
(d) withdrawing said carrier gas and all the volatiles from said headspace area of said canned tuna through said penetrating means other than the means utilized for the passing of said inert carrier gas into said container for analysis.

9. The method of claim 8 wherein said carrier gas is supplied at a flow rate of about 1 cc/min. to 100 cc/min.

10. The method of claim 8 wherein said canned tuna is submerged in water.

11. The method of claim 8 wherein said canned tuna is submerged in water at a temperature of about 25° C.

12. The method of claim 8 wherein said canned tuna is centrifuged at 900 X G before insertion of said first penetrating means.

13. The method of claim 8 wherein hydrogen sulfide gas is removed from the headspace of canned tuna.

14. A method of removing all the volatiles present in the headspace area of a sealed container for analysis without prematurely releasing the vacuum and said volatiles in said container comprising the steps of:
(a) inserting a first penetrating means into the headspace area of a sealed container,
(b) inserting a second penetrating means into said headspace area of said container,
(c) passing a first inert carrier gas into said headspace area of said container through said penetrating means,
(d) withdrawing said first inert carrier gas and all the volatiles from said headspace area of said container through said penetrating means other than the means utilized for this passing of said first inert carrier gas into said container,
(e) condensing said inert carrier gas and volatiles,
(f) heating said condensed first inert carrier gas and volatiles at a temperature sufficient to cause volatilization,
(g) flushing said volatiles with a second inert carrier gas through a chromatography detector.

15. The method of claim 14 wherein the first and second inert carrier gases are supplied at a flow rate of about 1 to about 100 cc/min.

16. The method of claim 14 wherein the first and second inert carrier gases are selected from the group consisting of nitrogen and helium.

17. The method of claim 14 wherein the sealed container is submerged in water.

18. The method of claim 14 wherein the sealed container is submerged in water at a temperature of about 70° C.

19. The method of claim 14 wherein said first inert carrier gas and the volatiles are heated at a temperature of about 130° C.

* * * * *